(12) United States Patent
Liu et al.

(10) Patent No.: US 8,781,075 B2
(45) Date of Patent: Jul. 15, 2014

(54) WIRELESS COMMUNICATION IN A MEDICAL IMAGING OR MONITORING SYSTEM

(75) Inventors: James Zhengshe Liu, Glenview, IL (US); Kenneth Kump, Waukesha, WI (US); Gireesha Rao, Pewaukee, WI (US); Chuande Liu, Waukesha, WI (US); Craig Dennis, Waukesha, WI (US)

(73) Assignee: General Electric Company, Schenectady, NY (US)

(*) Notice: Subject to any disclaimer, the term of this patent is extended or adjusted under 35 U.S.C. 154(b) by 606 days.

(21) Appl. No.: 12/986,943

(22) Filed: Jan. 7, 2011

(65) Prior Publication Data

US 2012/0177183 A1 Jul. 12, 2012

(51) Int. Cl.
*H05G 1/56* (2006.01)
*H05G 1/58* (2006.01)
*H05G 1/64* (2006.01)

(52) U.S. Cl.
USPC ............................ 378/114; 378/98.8; 378/116

(58) Field of Classification Search
USPC ............ 378/91, 98, 98.8, 114–116, 189, 204, 378/207, 210, 901; 370/201, 229–240, 242, 370/252, 248, 310, 312, 328–330, 345, 350, 370/431, 432, 437, 462, 463, 546; 719/319, 719/310; 375/224–228, 354–361, 377
See application file for complete search history.

(56) References Cited

U.S. PATENT DOCUMENTS

| | | | |
|---|---|---|---|
| 5,828,655 A * | 10/1998 | Moura et al. ................. | 370/236 |
| 6,201,890 B1 | 3/2001 | Shi et al. | |
| 6,215,853 B1 | 4/2001 | Kump et al. | |
| 6,343,111 B1 | 1/2002 | Avinash et al. | |
| 6,460,003 B1 | 10/2002 | Kump et al. | |
| 6,633,657 B1 | 10/2003 | Kump et al. | |
| 6,694,047 B1 | 2/2004 | Farrokhnia et al. | |
| 6,704,440 B1 | 3/2004 | Kump | |
| 7,221,782 B1 | 5/2007 | Kump | |
| 7,324,628 B2 | 1/2008 | Liu et al. | |
| 7,414,565 B2 | 8/2008 | Liu et al. | |
| 7,433,446 B2 * | 10/2008 | Abe ............................. | 378/114 |
| 7,488,947 B1 | 2/2009 | Petrick et al. | |
| 7,649,979 B2 | 1/2010 | Liu et al. | |
| 7,755,059 B2 | 7/2010 | Liu et al. | |
| 7,798,476 B2 | 9/2010 | Utschig et al. | |
| 7,807,977 B2 | 10/2010 | Xue et al. | |
| 2006/0213845 A1 | 9/2006 | Utshig et al. | |
| 2006/0242268 A1 | 10/2006 | Omernick et al. | |
| 2008/0029707 A1 * | 2/2008 | Kari et al. ................ | 250/370.09 |
| 2009/0040989 A1 * | 2/2009 | da Costa et al. ............. | 370/338 |
| 2009/0262709 A1 * | 10/2009 | Mason et al. ................ | 370/336 |

* cited by examiner

*Primary Examiner* — Anastasia Midkiff
(74) *Attorney, Agent, or Firm* — Fletcher Yoder P.C.

(57) ABSTRACT

The present disclosure is directed towards a method of changing wireless communication channels in a connected host and client system. For example, in one embodiment, the link quality of a connection is monitored by the host or the client. If the connection has a link quality below a predetermined threshold but remains intact, a channel switch request is sent, synchronization packages are exchanged between the host and client on the current channel, the channel of the system is changed to a new channel, and the system resumes communications on the new channel.

20 Claims, 7 Drawing Sheets

WIRELESS COMMUNICATION IN A MEDICAL IMAGING OR MONITORING SYSTEM

BACKGROUND OF THE INVENTION

The subject matter disclosed herein relates to medical imaging and patient monitoring systems that use wireless communication to exchange data between host and client devices within the system.

In current wireless medical imaging environments, X-ray imaging systems typically include an imaging subsystem base station and a detector. The imaging subsystem may be a fixed or mobile base station host and may employ one or more detachable or wireless detector clients. Similarly, wireless patient monitoring systems include a patient monitoring base station host that may communicate with one or more wireless sensor clients. For most wireless communication standards, including Wi-Fi and ultra-wide band (UWB), the total allowed frequency range for the standard is divided into various channels that are each represented by a respective channel number. Each channel operates relatively independently of the others, allowing devices to be configured to use specific channels within the standard to limit interference with one another during communication. Both the total frequency range and individual channels within the range may be regulated and allowed or disallowed by local governing bodies in a particular geographic region.

Like many methods of communication, wireless data connections are subject to potentially noisy channels as a result of environmental electromagnetic interference. Environmental noise can be a particular problem in the hospital setting, where numerous pieces of electrical equipment and wireless communication devices are operating in close proximity to one another. To further exacerbate the problem, the data throughput requirements for wireless medical systems can be at times both sizable and inflexible.

As the quality of a wireless connection between a host and a client begins to degrade due to channel noise, bits of data within data packages can be interpreted erroneously upon receipt due to the effects of noise on the data signal. While various data checking and verification schemes allow such errors to be detected, detecting such an error will result in a request for, and a resend of, the entire erroneous data package, lowering the data throughput of the system as a result of the additional overhead.

BRIEF DESCRIPTION OF THE INVENTION

In accordance with one embodiment, a method for changing wireless communication channels in a connected host and client system is presented. In the method, the link quality of a connection is continuously monitored by the host or the client. If the connection has a link quality below a predetermined threshold but remains intact, a channel switch request is sent, synchronization packages are exchanged between the host and client on the current channel, the channel of the system is changed to a new channel, and the system resumes communications on the new channel.

In accordance with another embodiment, an imaging host device is provided. The device includes, among other features, an X-ray source, circuitry configured to control the emission of radiation from the X-ray source, and one or more wireless communication interfaces. The wireless interfaces include circuitry configured to exchange data with detector clients, continuously monitor the link quality of the connection to a detector client and determine if the connection is intact. If the connection has a link quality is below a predetermined threshold but is still intact, a channel switch request is sent to the client, synchronization packages are exchanged between the host and client on the current channel, the channel of the system is changed to a new channel, and the system resumes communications on the new channel.

In accordance with another embodiment, a portable client device is presented. The device includes, among other features, one or more wireless communication interfaces. These wireless interfaces include circuitry being operable to exchange data with a base station host, continuously monitor the link quality for the wireless connection to a host and determine if the connection remains intact. If the circuitry determines that the connection has a link quality below a predetermined threshold but remains intact, a channel switch request is sent to the host, and then the connection is dropped. The circuitry is also operable to, if a channel switch request is received from a host, exchange a number of synchronization packages with the host on the current channel, and then resume system communications on a new channel.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present disclosure is directed towards wireless medical imaging and patient monitoring systems. Since wireless communication systems are subject to noisy channel communication issues, the link quality of a particular wireless communication channel may become poor enough that continuing system communication on that channel becomes impractical. In accordance with the present disclosure, one or both of the client or host devices of the wireless system monitor the link quality of the current wireless connection to determine if it is outside of an acceptable range. If the link quality of the connection is beyond a predetermined threshold or the connection is dropped, the system migrates communications to a different channel.

Figure 1:
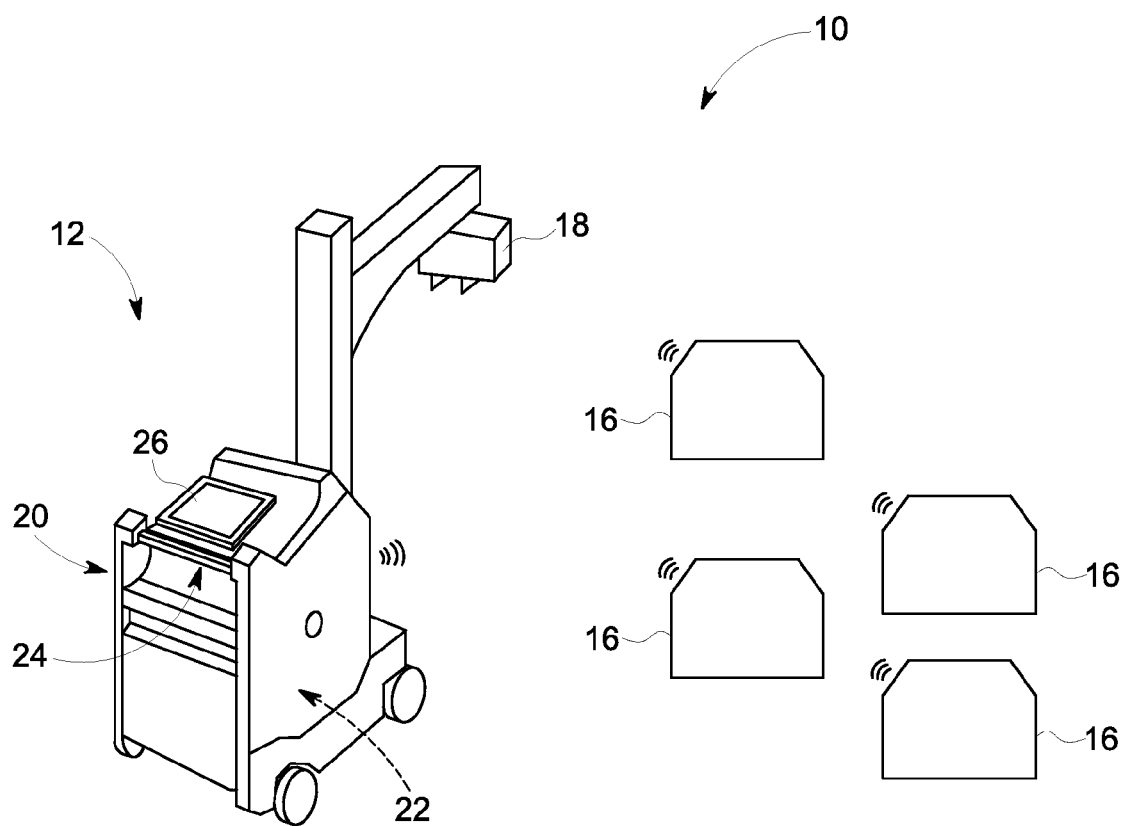
FIG. 1 is a perspective view of a wireless X-ray system, in accordance with aspects of the present disclosure.

Referring generally to FIG. 1, a wireless X-ray system is represented, referenced generally by reference numeral 10. In the illustrated embodiment, the wireless X-ray system 10 is a digital X-ray system designed both to acquire original image data and to process the image data for display. In the embodiment illustrated in FIG. 1, the wireless X-ray system 10 includes an X-ray base station 12 suitable for communicating with multiple digital X-ray detectors 16 located within the operative range of the X-ray base station 12. The X-ray system 10 is configured to coordinate operation of digital X-ray detectors 16. The X-ray base station 12 may be a mobile imaging system or a fixed imaging system. The X-ray base station 12 has an X-ray source 18 and, in conjunction with the digital X-ray detectors 16, is operable to perform X-ray imaging. The X-ray base station 12 may recognize and communicate with the multiple X-ray detectors 16.

In the depicted embodiment, the multiple detectors 16 are in communication with a base unit 20. The base unit 20 houses electronic circuitry 22 to wirelessly detect and communicate with the detectors 16, acquire image data from the detectors, and process the data to form desired images. In addition, the electronic circuitry 22 both provides and controls power to the X-ray source 18. The base unit 20 also has an operator workstation 24 that enables a user operate the wireless X-ray system 10 and monitor various system activities on display 26. In one embodiment, in order to wirelessly detect and communicate with the detectors 16, the electronic circuitry 22 and the detectors 16 all possess one or more wireless communication interfaces. In one such embodiment, all wireless interfaces in the base unit 20 and detectors 16 are provided a list of allowed wireless communication channels (i.e. frequencies) that are approved for a particular geographic region.

Figure 2:
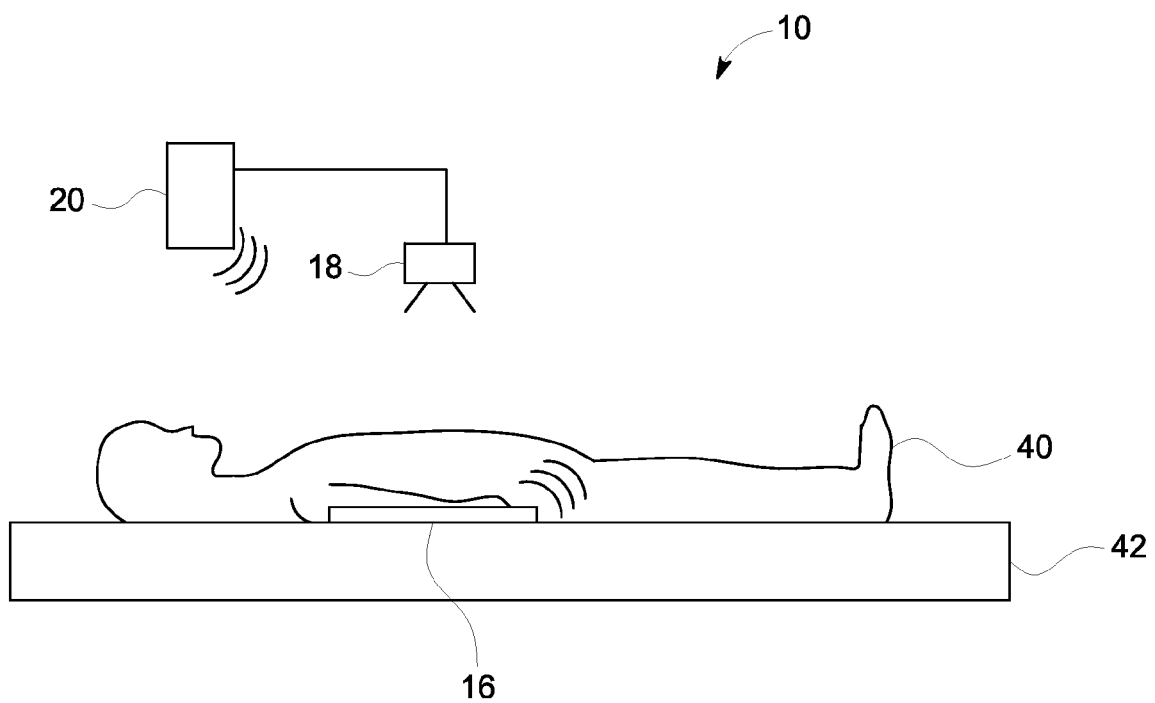
FIG. 2 is a diagrammatical side view of a wireless X-ray system with a patient, in accordance with aspects of the present disclosure.

In the embodiment of the wireless X-ray system 10 illustrated in FIG. 2, a patient 40 may be positioned between the X-ray source 18 and a detector 16. The patient 40 is placed on a table 42 underneath the X-ray source 18. The system 10 also includes a detector 16 positioned underneath the patient 40. During an imaging sequence, the detector 16 receives X-rays that pass through the patient and wirelessly transmits imaging data to a base unit 20 for processing.

Figure 3:
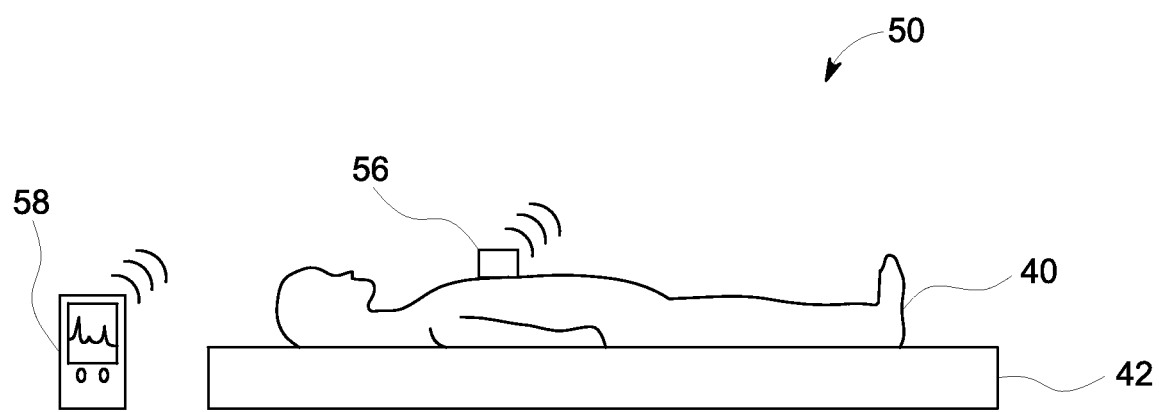
FIG. 3 is a diagrammatical side view of a wireless patient sensor and a wireless patient monitoring base station being used with a patient, in accordance with aspects of the present disclosure.

In other embodiments, other types of systems may be configured to communicate wirelessly in accordance with the present disclosure. For example, referring to FIG. 3, a wireless patient monitoring system is represented, referenced generally by reference number 50. In the illustrated embodiment, the wireless patient monitoring system 50 is operable to monitor physical attributes of a patient 40 lying on table 42 using a wireless patient sensor 56 and transmit this data to a patient monitoring base station 58 for processing and display. Accordingly, the wireless patient sensor 56 includes circuitry operable to detect patient temperature, blood pressure, heart rate, and the like. The wireless patient monitoring base station 58 includes circuitry operable to process patient data, determine if any patient attributes are beyond an acceptable level, sound appropriate alarms, and display the processed patient data on a screen. In order to wirelessly communicate, the patient monitoring base station 58 and the sensor 56 possess one or more wireless communication interfaces as discussed herein. In one such embodiment, wireless interfaces are provided a list of allowed wireless communication channels that are approved for a particular geographic region.

In one implementation, during the operation of a wireless X-ray system 10 or a patient monitoring system 50, the base stations 12 and 58 serve as wireless host devices, and the detectors 16 and sensors 56 serve as wireless client devices, for their respective embodiments. In each embodiment, the host and client wirelessly communicate with one another on a certain channel. However, the channel may become too noisy to continue communications on the current channel, requiring the system to change to a new channel in order to resume the data exchange. To determine if the current channel has become too noisy to continue communications, one or more particular link quality metrics may be monitored in real time to determine when they have fallen below a predetermined threshold. These metrics may include, but are not limited to, signal to noise ratio, signal strength, absolute or relative number (e.g., percentage) of packages that fail data verification, and absolute or relative number (e.g., percentage) of dropped packages. One or more metrics may be monitored by either or both the host or the client device within the system. The predetermined value of a particular threshold may be determined based on the data throughput and delay requirements and limitations for a particular activity.

Figure 4:
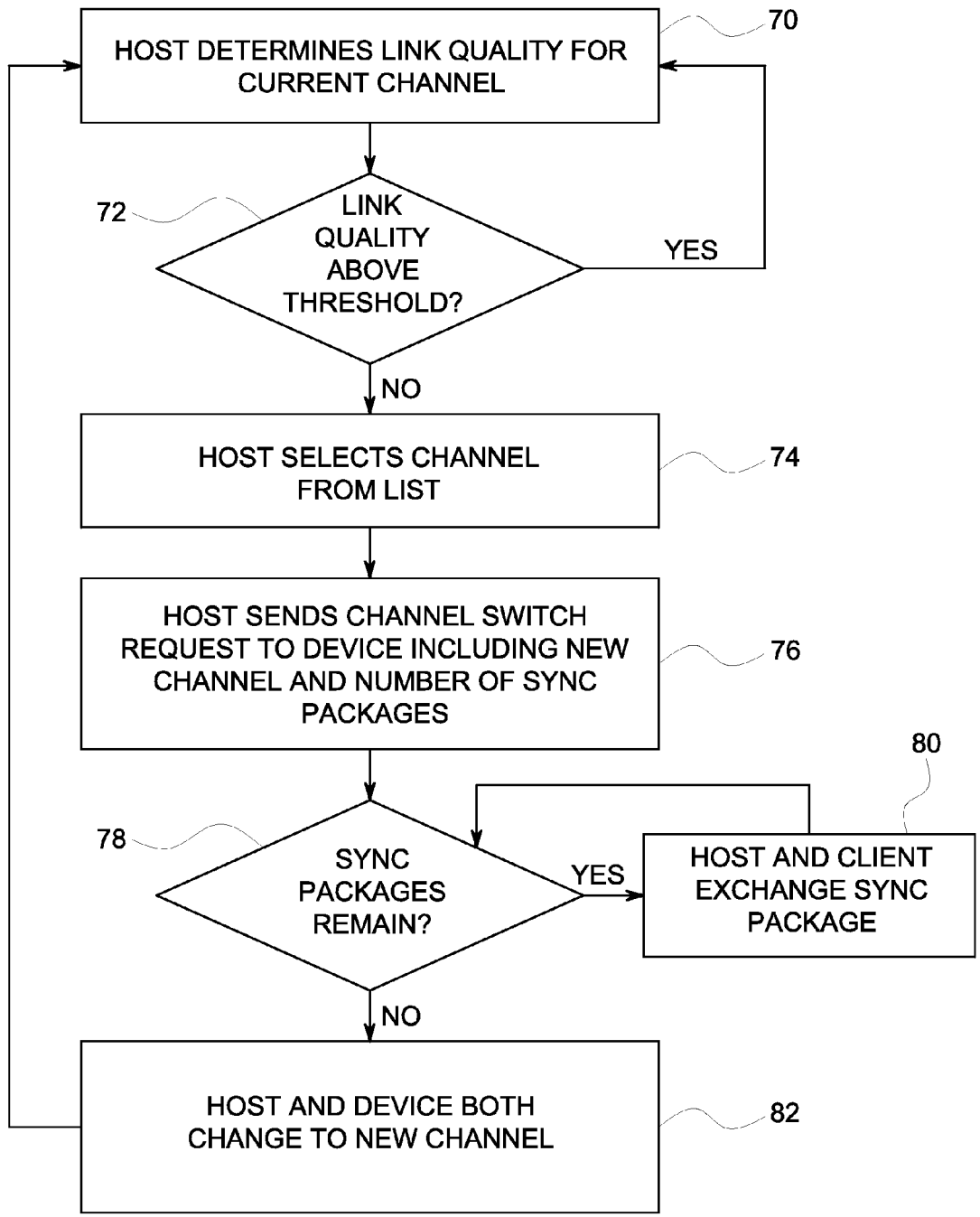
FIG. 4 is a flow diagram of an embodiment in which the host monitors the quality of the link, in accordance with aspects of the present disclosure.

FIG. 4 illustrates one embodiment of a channel change method for a host and client system, where the host is responsible for monitoring (block 70) the link quality of the connection. When the link quality of the system has fallen below a predetermined threshold (block 72), the host selects (block 74) a new channel and then sends (block 76) a channel switch request to the client. In the depicted implementation, the channel switch request includes at least the selected channel and a numerical value representing the number of synchronization packages to be exchanged. While synchronization packages remain to be exchanged (block 78), synchronization packages are sent (block 80) from the host to the client specifying the number of synchronization remaining, while the client replies back to the host with a synchronization package having the same numerical value. This count of remaining synchronization packages effectively serves as a count-down, and once the host and the client have each sent a final synchronization package signifying the end of the count-down, both devices switch (block 82) to the new channel to resume communications. After switching channels, the host resumes monitoring (block 70) the link quality of the connection on the new channel.

Figure 5:
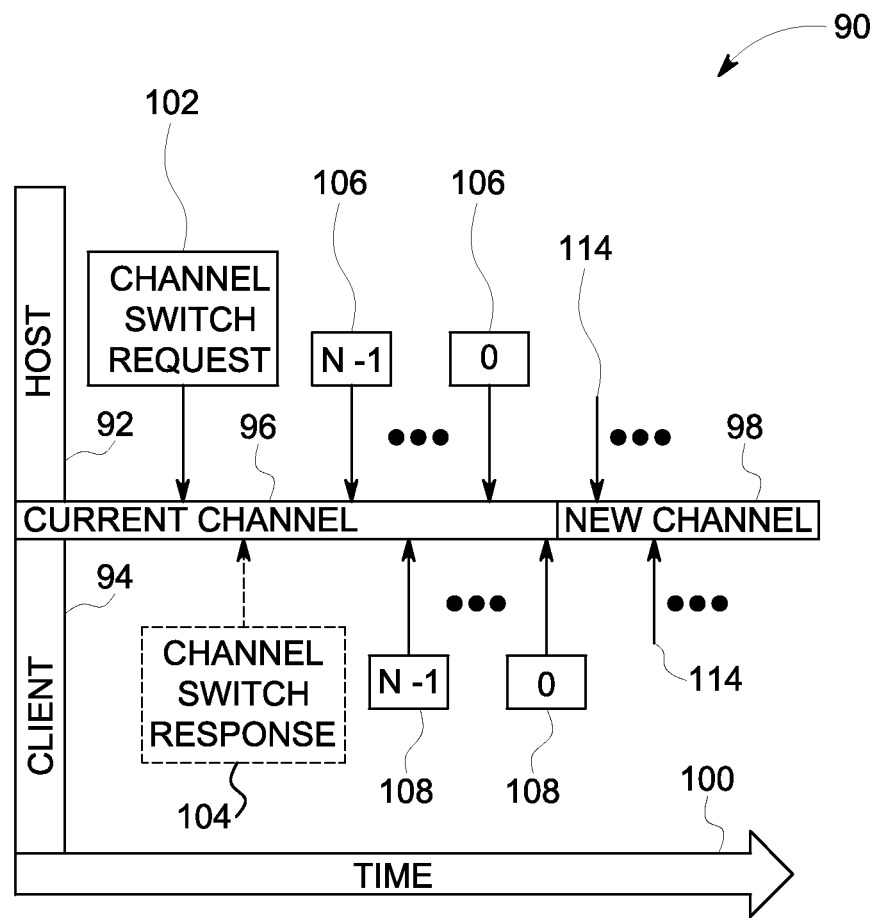
FIG. 5 is a timeline view of client and host activities for the embodiment illustrated by FIG. 4.

FIG. 5 depicts a timeline 90 for the embodiment illustrated by FIG. 4. In the timeline 90, there are communication packages being sent between a host 92 and a client 94 on either the current channel 96 or the new channel 98 over time 100. When the host 92 monitoring the link quality of the current connection determines that the link quality has fallen below a predetermined threshold, the host 92 selects a new channel 98 and then sends a channel switch request 102 to the client. In one embodiment, the channel switch request 102 specifies the selected channel number and a numerical value representing the number of synchronization packages to be exchanged. The client 94 optionally responds with a channel switch response 104 to confirm receipt of the request 102. In the depicted implementation, the host sends to the client a series of synchronization packages 106 having the numerical value of synchronization packages remaining, waiting between each synchronization package for a client response 108. After the receipt of each synchronization package 106 from the host 92, the client 94 replies back to the host 92 with a synchronization package 108 having the same numerical value received. In one embodiment, once the synchronization package with the final count-down value (e.g., 0) has been sent by the host 92 and the client 94, both devices change to the new channel 98 and resume normal system communications 114 on the new channel 98.

Figure 6:
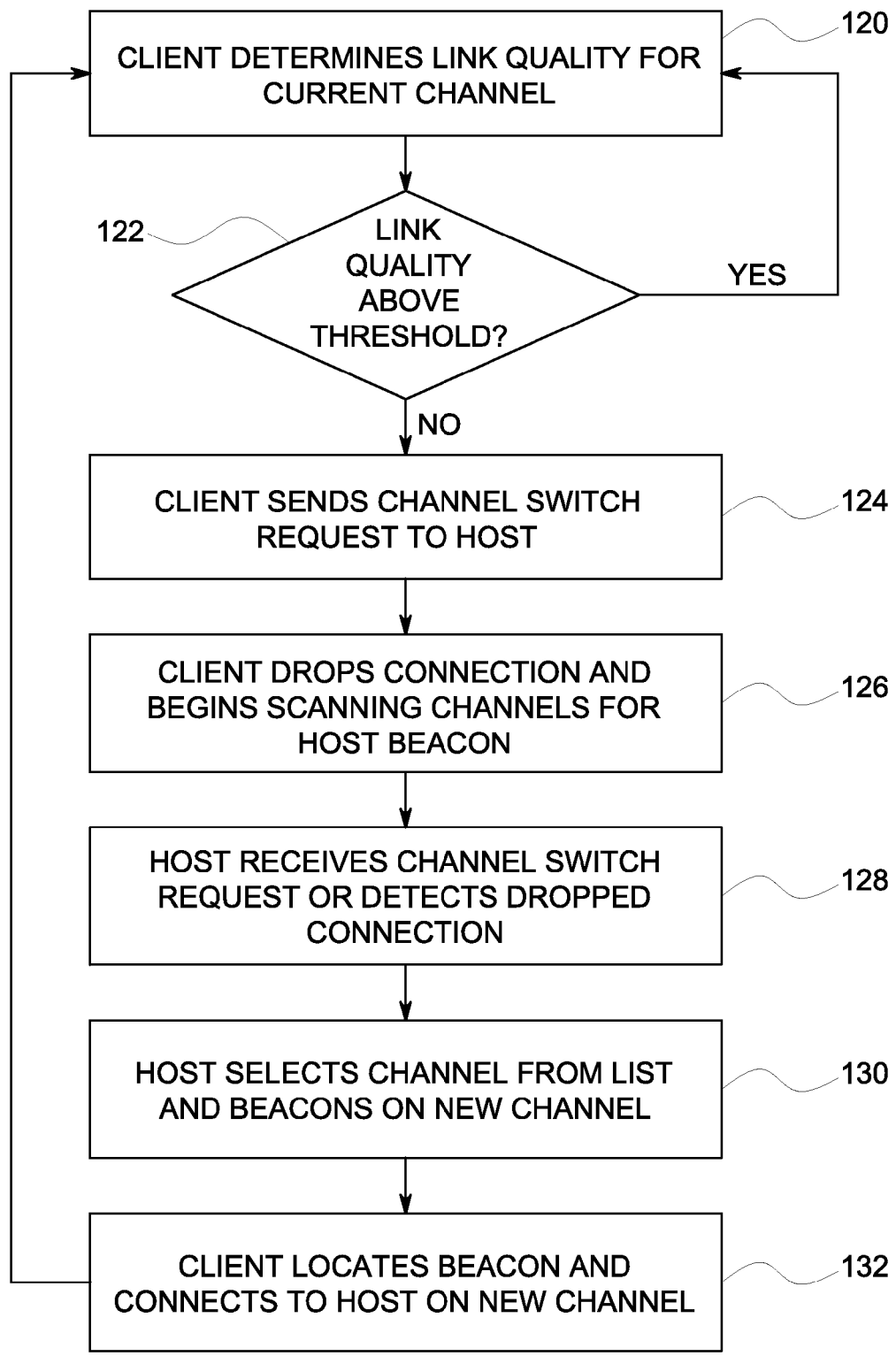
FIG. 6 is a flow diagram of an embodiment in which the client monitors the quality of the link, in accordance with aspects of the present disclosure.

Referring generally to figure FIG. 6, another embodiment of the channel change method between a host and client device is illustrated. In this embodiment, the client is responsible for monitoring (block 120) the link quality of the wireless connection. When the client determines (block 122) that the link quality of the current connection has fallen below a predetermined threshold, the client sends (block 124) a channel switch request to the host, drops the connection to the host, and continually scans (block 126) channels looking for the beacon of a host. The host, upon receipt of the channel switch request or upon detecting the dropped connection (block 128), selects a new channel and broadcasts (block 130) a beacon on this new channel. The client, upon locating the beacon of the host on the new channel, connects (block 132) to the host on the new channel. After connecting, the client resumes monitoring (block 120) the link quality of the new connection on the new channel.

Figure 7:
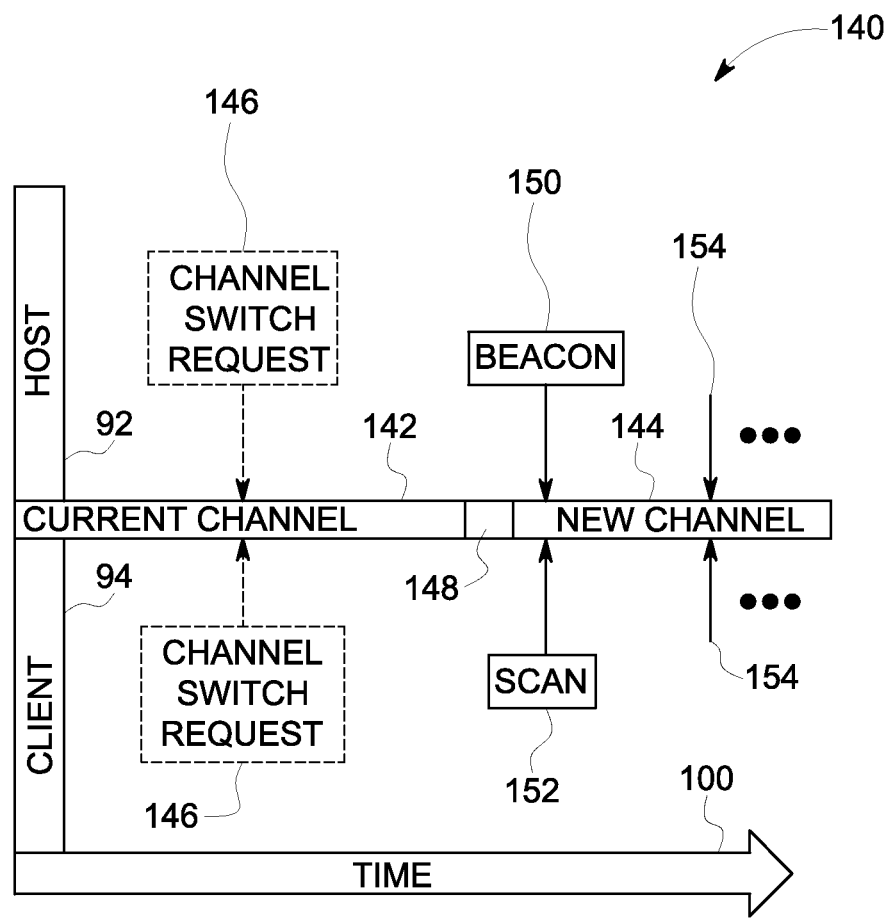
FIG. 7 is a timeline view of client and host activities for an embodiment similar to that illustrated by FIG. 6, in accordance with aspects of the present disclosure.

FIG. 7 depicts a timeline 140 for an embodiment similar to the one illustrated by FIG. 6. In this embodiment, either or both of the host 92 or the client 94 is responsible for monitoring the link quality of the current connection on the current channel 142 over time 100. When a device responsible for monitoring the link quality determines that it has fallen below a predetermined threshold for the current connection, that device may send to the other device a channel switch request 146 and then drop the connection, producing a temporary lapse in system communication 148. In one embodiment, the host 92, having detected a channel switch request 146 from the client 94 or the dropped connection 148, selects a new channel 144 and begins to broadcast a beacon 150 on the new channel. The client 94, having dropped the connection 148 or detected the drop of the connection 148, begins to continuously scan channels 152 looking for beacon 150 of the host 92. When the client 94 locates the beacon 150 of the host 92 on the new channel 144, the host 92 and client 94 reconnect on the new channel 144 to resume normal system communications 154.

Alternatively, in another embodiment, neither the host 92 nor the client 94 sends a channel switch request 146 to the other device before the connection is lost 148. In such an embodiment, the host 92, having detected the dropped connection 148, selects a new channel 144 and begins to broadcast a beacon 150 on the new channel. The client 94, having detected the drop of the connection 148, begins to continuously scan channels 152 looking for beacon 150 of the host 92. When the client 94 locates the beacon 150 of the host 92 on the new channel 144, the host 92 and client 94 reconnect on the new channel 144 to resume normal system communications 154.

Technical effects of the invention include the ability of a wireless medical system to effectively monitor the link quality of a wireless connection and migrate system communication to a different wireless channel if the link quality is below a predetermined threshold or the connection is dropped. Further, the present disclosure allows for increased data throughput and reliability of communications in wireless medical systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for changing wireless communication channels in a connected host and client system comprising:
    sending and receiving data via a connection;
    monitoring the link quality of the connection and determining if the connection remains intact;
    when the connection has a link quality below a predetermined threshold but remains intact, performing operations comprising:
        sending a channel switch request and receiving a channel switch response via the connection,
        changing the channel of the system to a new channel, and
        resuming system communication on the new channel.

2. The method of claim 1, wherein the link quality is determined by the host or client monitoring one or more of signal to noise ratio, signal strength, number of packages failing data verification, or number of dropped packages.

3. The method of claim 1, wherein the channel switch request indicates the new channel to which the requestor intends to change.

4. The method of claim 1, wherein the channel switch request indicates a number of synchronization packages to be exchanged before changing to the new channel.

5. The method of claim 4, wherein, exchanging synchronization packages comprises:
    the host successively delivering synchronization packages to the client, each synchronization package comprising a decrementing count of the number of synchronization packages remaining, and
    the host successively receiving the synchronization packages back from the client until the count of the number of synchronization packages remaining has reached the count-down target.

6. The method of claim 1, wherein either the host or client device drops the connection to the other device after sending the channel switch request.

7. The method of claim 1, wherein, when the connection does not remain intact, operations are performed, comprising:
    the host device selecting the new channel and broadcasting a beacon on the new channel,
    the client device scanning channels until the new channel is located where the beacon of the host is detected, and
    the host and client reconnecting on the new channel to resume system communication.

8. An imaging host device comprising:
    an X-ray source;
    circuitry configured to control the emission of radiation from the X-ray source;
    one or more wireless communication interfaces comprising circuitry configured to:
        exchange data with a detector client over a connection;
        monitor a link quality of the connection to the detector client and determine if the connection remains intact;
        when the link quality of the connection is below a predetermined threshold but remains intact, perform operations comprising:
            sending a channel switch request to the detector client via the connection,
            receiving a channel switch response from the detector client via the connection,
            establishing a new connection on a new wireless channel based on the channel switch request, and
            resuming system communication via the new connection.

9. The device of claim 8, wherein the channel switch request indicates a new channel number corresponding to the new channel selected by the host.

10. The device of claim 8, wherein the channel switch request indicates a number of synchronization packages to be exchanged before changing to the new channel.

11. The device of claim 10, wherein, exchanging synchronization packages comprises the host successively delivering a synchronization package to the detector client, and then receiving a synchronization package response from the detector client until a count of the number of synchronization packages remaining has reached a count-down target.

12. The device of claim 8, wherein the host drops the connection to the detector client after sending the channel switch request to the detector client.

13. The device of claim 8, wherein, when the connection does not remain intact, a series operations are performed comprising:
    selecting the new channel, and
    continuously broadcasting a beacon on the new channel until it is located by the detector client, and
    connecting to the detector client on the new channel.

14. A portable client device comprising wireless communication circuitry configured to:
    exchange data with a host via a wireless connection;
    monitor a link quality of the wireless connection to the host and determine if the connection remains intact;
    when the wireless connection has a link quality below a predetermined threshold but remains intact, send a channel switch request to the host via the wireless connection; and
    when the channel switch request is received by the host, exchange a number synchronization packages with the host on the current channel, change to a new channel specified in the channel switch request, and then resume exchanging data with the host on the new channel.

15. The device of claim 14, wherein the client device is a portable X-ray detector client comprising circuitry configured to detect and transduce emissions from a radiation source into a portion of the data exchanged with the host.

16. The device of claim 14, wherein the client device is a portable patient sensor client comprising circuitry configured to perform measurements of physical attributes of a patient, wherein these measurements comprise a portion of the data exchanged with the host.

17. The device of claim 14, wherein a channel switch request received from the host comprises one or both of a new channel number corresponding to the new channel or the number of synchronization packages to be exchanged.

18. The device of claim 14, wherein, exchanging synchronization packages comprises the client device successively receiving a synchronization package from the host and then sending a synchronization package response back to the host until a number of synchronization packages remaining equals a count-down target.

19. The device of claim 14, wherein the client device drops the wireless connection to the host after sending the channel switch request to the host.

20. The device of claim 14, wherein, when no wireless connections to the host are currently present, the wireless communication circuitry is configured to perform a series of operations comprising:
    searching different channels until an active channel with a beacon from the host is located, and
    connecting to the beaconing host on the active channel, and resuming exchanging data with the host via the active channel.

* * * * *